United States Patent [19]

Bay et al.

[11] Patent Number: 4,814,467

[45] Date of Patent: Mar. 21, 1989

[54] PROCESSES USING A PHOSPHORUS COMPLEX

[75] Inventors: Elliott Bay; Andrea Leone-Bay, both of Ridgefield, Conn.; Peter E. Timony, Valley Cottage, N.Y.

[73] Assignee: ICI Americas Inc., Wilmington, Del.

[21] Appl. No.: 146,944

[22] Filed: Jan. 22, 1988

Related U.S. Application Data

[63] Continuation-in-part of Ser. No. 58,107, Jun. 4, 1987, abandoned, and Ser. No. 44,162, Apr. 30, 1987, abandoned, which is a continuation-in-part of Ser. No. 26,311, Mar. 16, 1987, Pat. No. 4,727,194, said Ser. No. 58,107, is a continuation-in-part of Ser. No. 44,162, , Ser. No. 947,798, Dec. 29, 1986, Pat. No. 4,785,121, and Ser. No. 26,311.

[51] Int. Cl.$^4$ ............................................. C07D 307/89
[52] U.S. Cl. ..................... 549/246; 564/412; 570/196; 570/201; 570/261
[58] Field of Search ....................... 570/196, 201, 261; 564/412; 549/246

[56] References Cited

U.S. PATENT DOCUMENTS 4,634,771  1/1987  Shim et al. ............................ 546/286

OTHER PUBLICATIONS

Zhmurova et al, Org. Phos. Comp. Ref., vol. 3, 705, Monatsh, 70 (1937) pp. 1–19.

Fedorova et al, Zhur. Obshchei. Khim., vol. 30 (1960) pp. 4044–4048.

Primary Examiner—Richard L. Raymond
Attorney, Agent, or Firm—Harry A. Pacini

[57] ABSTRACT

A process for chlorinating compounds containing a carbon atom bonded to a hetero-atom selected from the group consisting of oxygen, nitrogen and sulfur; said process comprises contacting the carbon hetero-atom containing compound with a chloro phosphorus complex of the formula

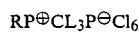

$$RP^{\oplus}CL_3P^{\ominus}Cl_6$$

wherein R is selected from the group consisting of aryl, substituted aryl, alkyl and substituted alkyl, so that the hetero-atom is replaced by at least one chlorine atom; compounds capable of being chlorinated can include, for example, carboxylic acids, acid chlorides, ketones, aldehydes, alcohols, epoxides, esters, anhydrides, ethers, thiols, and aromatic nitro groups; the reaction can be extended to compounds containing the carbon to chlorine bond alpha to a carbon atom containing at least one hydrogen atom, it can be further dehydrochlorinated, e.g., by either heating to a temperature ranging from about 50° C. to about 300° C. or by reaction with a base selected, e.g., from alkali metal hydroxides and alkoxides.

10 Claims, No Drawings

PROCESSES USING A PHOSPHORUS COMPLEX

CROSS-REFERENCE TO RELATED APPLICATIONS

This application is a continuation-in-part of U.S. Ser. No. 044,162, filed Apr. 30, 1987, now abandoned, which is a continuation-in-part of U.S. Ser. No. 026,311, filed Mar. 16, 1987, entitled "Preparation of a Phosphorus Complex", now U.S. Pat. No. 4,727,194.

This application is also a continuation-in-part application of U.S. Ser. No. 058,107, filed June 4, 1987, now abandoned, which is a continuation-in-part application U.S. Ser. No. 044,162, filed Apr. 30, 1987, now abandoned; U.S. Ser. No. 947,798, filed Dec. 29, 1986, now U.S. Pat. No. 4,785,121; and U.S. Ser. No. 026,311, filed Mar. 16, 1987, now U.S. Pat. No. 4,727,194.

BACKGROUND OF THE INVENTION

1. Field of the Invention

This invention relates to a process for chlorinating and dehydrochlorinating certain organic compounds and, in particular, a process for using a phosphorus complex, e.g., phenyltrichlorophosphonium hexachlorophosphate as a reactant.

2. Related Information

The phosphorus complex useful in the process of this invention is exemplified by the compound phenyltrichlorophosphonium hexachlorophosphate. This compound is known in the art and has heretofore been used in the preparation of certain phosphorus-containing compounds.

The article entitled "Reaction of Phosphorus Pentachloride With Unsaturated Hydrocarbons" by G. K. Fedorova et al., *Zhur. Obshchei. Khim.* 30 4044 (1960), reported the reaction of styrene with phosphorus pentachloride to form a colorless complex with the structure

This reference further disclosed that styrylphosphonous dichloride is formed when the complex is reacted with $SO_2$. With styrene, the complex forms styrylphosphorus tetrachloride, and on reduction with red phosphorus, the complex is converted into styryldichlorophosphine. However, this reference does not disclose the unique processes of this invention.

In the article entitled "Tetrachloro-(m- and p-nitrophenyl) Phosphoranes" by I. N. Zhmurova et al., *Org. Phos. Comp. Ref.*, 705, Vol. 3, Monatsh. 70, 1–19 (1937), the reaction disclosed in the previous reference was cited for preparing a phosphorus complex. This reference disclosed the treatment of

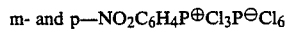

with red phosphorus at a molar ratio of 3:2 to obtain tetrachloro-(nitrophenyl)phosphoranes. Again, this reference does not disclose the unique processes of this invention.

U.S. Pat. No. 4,634,771, Shim et al., Jan. 6, 1987, disclosed the reaction of carboxylic acid groups on aromatic ring compounds with phenylphosphonous dichloride, chlorine, and phosphorus trichloride to convert the carboxylic acid groups to trichloromethyl groups. This reference distinguished the use of phosphorus pentachloride and suggested that phosphorus pentachloride is specific for the conversion of a carboxylic acid group adjacent, or alpha, to the hetero-atom of an N-heteroaromatic (N=nitrogen) compound. However, this reference did not disclose the use of the phosphorus complex exemplified by phenyltrichlorophosphonium hexachlorophosphate that is used in the process of this invention.

U.S. Pat. No. 4,419,514, McKendry et al., Dec. 6, 1983, disclosed a method for converting carboxylic acid groups to trichloromethyl groups which comprises contacting a compound containing a carboxylic acid group with phenylphosphonic dichloride and phosphorus pentachloride at a specified molar ratio for a time and at a temperature sufficient to carry out the conversion of a carboxylic acid group to a trichloromethyl group. However, this reference does not disclose the use of a phosphorus complex as the chlorinating agent. In fact, this reference teaches that it is helpful to allow the carboxylic acid compound and the phenylphosphonic dichloride compound to react for a period of time (until HCl evolution ceased) before adding the phosphorus pentachloride.

U.S. Pat. No. 4,167,525, Kataoka et al., Sept. 11, 1979, disclosed the preparation of aromatic acyl chlorides by reacting an aromatic carboxylic acid, phosphorus trichloride, and chlorine to produce phosphorus pentachloride in situ which is then treated with either water or certain phosphorus compounds to convert the phosphorus pentachloride into phosphorus oxychloride. The resulting reaction mixture is then distilled to obtain phosphorus oxychloride and, successively, the desired aromatic acyl chloride. The process of this reference improves prior known processes by allowing the preparation of the aromatic acyl chloride without causing blocking of the distillation equipment by phosphorus pentachloride and without formation of troublesome by-products. However, this reference does not disclose the use of a phosphorus complex as disclosed in the process of this invention.

SUMMARY OF THE INVENTION

An object of this invention is to provide a process for simply chlorinating compounds containing a carbon atom bonded to a hetero-atom selected from the group consisting of oxygen, nitrogen and sulfur. A further object of this invention is to provide a process for reacting compounds containing a carbon atom alpha to a carbon atom containing at least one hydrogen atom and bonded to a hetero-atom selected from the group consisting of oxygen, nitrogen and sulfur.

Other objects and advantages of the present invention are described elsewhere within the specification.

This invention is a process for chlorinating a compound containing a carbon atom bonded to a hetero-atom selected from the group consisting of oxygen, nitrogen and sulfur, which comprises contacting the compound with a chloro phosphorus complex of the formula

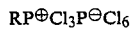

wherein R is selected from the group consisting of aryl, substituted aryl, alkyl and substituted alkyl so that the hetero-atom is replaced by at least one chlorine atom.

This invention further discloses a process for reacting a compound containing a carbon atom alpha to a carbon atom containing at least one hydrogen atom and bonded to a hetero-atom selected from the group consisting of oxygen, nitrogen and sulfur which comprises (a) contacting the compound with a chloro phosphorus complex of the formula $$RP^{\oplus}Cl_3P^{\ominus}Cl_6$$

wherein R is selected from the group consisting of aryl, substituted aryl, alkyl and substituted alkyl so that the hetero-atom is replaced by at least one chlorine atom. The reaction can take place with or without the use of a non-reactive suitable solvent. Suitable solvents must of necessity be at the reaction conditions, high boiling and the reactants must be soluble therein. For example, chlorobenzenes and the like are suitable.

(b) The process may be extended to dehydrochlorinate the chlorine-containing compound formed in step (a). In this process, the chlorine-containing compound can be dehydrochlorinated by heating to a reaction temperature ranging from about 50° to about 300° C. or, alternatively, by contacting the compound containing said bond with a base preferably selected from the group consisting of alkali metal hydroxides and alkoxides. The dehydrochlorination reaction may take place with or without a suitable solvent.

DETAILED DESCRIPTION OF THE INVENTION

In the process of this invention, the hetero-atom in a carbon to hetero-atom bond is replaced with a chlorine atom to form a carbon to chlorine bond. This compound containing the carbon to chlorine bond can further be dehydrochlorinated when said compound contains a second carbon atom containing at least one hydrogen atom, alpha to the first carbon atom.

The compound containing the carbon atom bonded to the hetero-atom is exemplified by the listing of compounds in the following Table. The Table further lists the resulting chlorinated compound and, where appropriate, the resulting dehydrochlorinated compound.

TABLE 1

| No. | C—X Compounds | C—Cl Compounds | Dehydrochlorinated Compounds |
|---|---|---|---|
| 1 | $R^1$—OH | $R^1$—Cl | |
| 2 | $R^1$—CH(OH)—CH$_2R^1$ (with H) | $R^1$—CCl(H)—CH$_2R^1$ | $R$—C(H)=CH—R |
| 3 | $R^1$—COOH | $R^1CCl_3$ | |
| 4 | $R^1$—O—$R^1$ | $R^1$—Cl | |
| 5 | epoxide (R$^1$, R$^1$) | $R^1$—CHCl—CHCl—$R^1$ (shown as $R^1$—CH$_2$CH$_2R^1$ with two Cl) | $R^1$CH=CHR$^1$ & $R^1$C≡CR$^1$ |
| 6 | $R^1$—NO$_2$ | $R^1$—Cl | |
| 7 | $R^1$—C(=O)—$R^1$ | $R^1CCl_2R^1$ | |
| 8 | $R^1$—CH$_2$—C(=O)—CH$_2R^1$ | $R^1$CH$_2$—CCl$_2$—CH$_2R^1$ | $R^1$—C(H)=C=C(H)—$R^1$ |
| 9 | $R^1$CH=O | $R^1CCl_2H$ | |
| 10 | $R^1$C(=O)Cl | $R^1CCl_3$ | |
| 11 | $R^1$C(=O)—NH$_2$ | $R^1CCl_2$—NH$_2$ | $R^1CN$ |
| 12 | $R^1$—C(H)=NOH | | $R^1CN$ |

TABLE 1-continued

| No. | C—X Compounds | C—Cl Compounds | Dehydrochlorinated Compounds |
|-----|---------------|----------------|------------------------------|
| 13  | 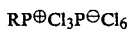 | 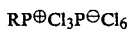 | |

$R^1$ in the above table is selected independently each time it occurs from the group consisting of $C_1$-$C_{24}$ straight and branched chained alkyl, $C_6$-$C_{10}$ aryl, and $C_6$-$C_{10}$ aryl substituted with one or more alkyl groups. The compounds listed in the above table are merely exemplary and are not meant to be inclusive of all compounds. The compounds listed under the column designated "C-X Compounds", exemplify certain compounds containing a carbon atom bonded to a heteroatom selected from the group consisting of oxygen, nitrogen and sulfur. The compounds listed under the column designated "C-Cl Compounds" represent certain of the chlorinated compounds that can result from the process of this invention. The compounds listed under the column designated "Dehydrochlorinated Compounds" represent some of the compounds that can result from the process of this invention.

In this invention, the compound containing the carbon atom bonded to the hetero-atom is chlorinated by contacting said compound with a chlorophosphorus complex. This chloro phosphorus complex is of the formula $$RP^{\oplus}Cl_3P^{\ominus}Cl_6$$

wherein R is selected from the group consisting of $C_6$-$C_{10}$ aryl; $C_6$-$C_{12}$ substituted aryl, wherein the substituent can comprise at least one member selected from the group consisting of nitro, chloro, fluoro, $C_1$-$C_6$ alkyl, $C_1$-$C_6$ fluoroalkyl, $C_1$-$C_6$ alkoxy and mixtures thereof; $C_1$-$C_6$ alkyl; and $C_1$-$C_6$ substituted alkyl. The substituents on the substituted alkyl can be selected from the group consisting of nitro, chloro, fluoro and mixtures thereof. The substituents listed above for both the substituted aryl and the substituted alkyl are merely preferred substituents and can include any non-interfering substituents. A preferred phosphorus complex results when R is phenyl with the resulting complex being phenyltrichlorophosphonium hexachlorophosphate. These chlorophosphorus complexes can be prepared by any of the known methods, but it is especially preferred to use the process described in the parent application.

The reaction of the chlorophosphorus complex with the compound containing the carbon to hetero-atom bond can take place in the presence of a solvent. A preferred solvent is phenylphosphonic dichloride. Additionally, the reaction can take place at various temperatures, depending upon the particular reactants. Increased temperatures will generally increase the rate of reaction and reduce the actual reaction time.

The compounds capable of being chlorinated by this chlorophosphorus complex are varied. When the hetero-atom is oxygen, these compounds can include alcohols, carboxylic acids, ketones, aldehydes, acetals, ketals, ethers, epoxides, acid chlorides, esters and mixtures thereof. When the hetero-atom is nitrogen, the compounds can include nitroaromatics, amides, oximes and mixtures thereof. When the hetero-atom is sulfur, the compounds can incude thiols, sulfoxides, sulfones, sulfonates and sulfides.

This invention further discloses a process for reacting a compound containing a carbon atom alpha to a carbon atom containing at least one hydrogen atom and bonded to a hetero-atom selected from the group consisting of oxygen, nitrogen and sulfur. In this process, this compound is first contacted with the chloro-phosphorus complex described above so that the hetero-atom is replaced by at least one chlorine atom, and then the carbon chlorine bond formed is dehydrochlorinated. When the hetero-atom is oxygen, the compound is dehydrated. When the hetero-atom is nitrogen, ammonia is eliminated, and when the hetero-atom is sulfur, hydrogen sulfide is eliminated.

The carbon chlorine bond formed can be dehydrochlorinated by any known method. In particular, this bond can be dehydrochlorinated by heating the reaction mixture to a reaction temperature ranging from about 50° C. to about 300° C. Additionally, the dehydrochlorination can be accomplished by contacting the compound containing the carbon chlorine bond with a base. The base is preferably selected from the group consisting of alkali metal hydroxides and alkali metal alkoxides.

The following experiments describe various embodiments of this invention. Other embodiments will be apparent to one of ordinary skill in the art from a consideration of this specification or practice of the invention disclosed herein. It is intended that the specification and experiments be considered as exemplary only, with the true scope and spirit of the invention being indicated by the claims which follow the experiments.

EXPERIMENTS

1. Trichlorophenylphosphonium hexachlorophosphide $$(C_6H_5P^{\oplus}Cl_3P^{\ominus}Cl_6)$$

was prepared according to either the procedcure disclosed by Fedorova et al. in *Zhur. Obshchei. Khim* 30, 4044 (1960) or the procedure disclosed in U.S. patent application Ser. No. 026,311, filed Mar. 16, 1986, entitled "Preparation of a Phosphorus Complex," now U.S. Pat. No. 4,727,194.

2. Representative Reaction of Aromatic Nitro Compounds with Trichlorophenylphosphonium Hexachlorophosphide A. Nitrobenzene To a mixture of trichlorophenylphosphonium hexachlorophosphide (18.5 g, 40.6 millimoles) in the solvent phenylphosphonic dichloride (100 ml) was added nitrobenzene (5.0 g, 40.6 mM). The yellow reaction mixture was heated to about 160° C. for 12 hours. After cooling to room temperature, the reaction mixture was poured onto ice and the resulting product extracted with ether three times. The combined organic extracts were washed with water and brine and dried over anhydrous magnesium sulfate. Removal of the ether by distillation gave chlorobenzene (4.2 g, 92 wt. % yield) as a yellow liquid.

B. 3-Nitrophthalic Anhydride

Phenyltrichlorophosphonium hexachlorophsphide (4 g, 8.8 mM) was added to phenylphosphonic dichloride (10 ml). To this solutoin, 3 nitrophthalic anhydride (1.7 g, 8.8 mM) was added. The reaction mixture was heated to 170° C. for 12 hours, then cooled to room temperature and poured onto ice. After neutralizing with 50% aqueous sodium hydroxide, the reaction was extracted with ethyl acetate. The combined ethyl acetate extracts were washed with brine, dried over magnesium sulfate, and concentrated in vacuo to give 3-chlorophthalic anhydride (1.3 g, 81 wt. % yield) as a tan solid.

3. Representative Reaction of Alcohols with Trichlorophenylphosphonium Hexachlorophosphide To a mixture of trichlorophenylphosphonium hexachlorophosphide (10.5 g, 22.9 mM) in the solvent phenylphosphonic dichloride (50 ml) was added 3-methyl-1-butanol (2.02 g, 22.9 mM). The reaction mixture was stirred at room temperature for 12 hours and worked-up as described above to give 3-methyl-1-chlorobutane (2.2 g, 91 wt. % yield) as a clear liquid.

4. Representative Reaction of Epoxides with Trichlorophenylphosphonium Hexachlorophosphide To a mixture of trichlorophenylphosphonium hexachlorophosphide (3.8 g, 8.3 mM) in the solvent phenylphosphonic dichloride (10 ml) was added 1,2-epoxyhexane (831 mg, 8.3 mM). The reaction mixture was stirred for 12 hours at room temperature and worked-up as described above to 1,2 dichlorohexane (678 mg, 53 wt. % yield) as a yellow liquid.

5. Representative Reaction of Carboxylic Acids with Trichlorophenylphosphonium Hexachlorophosphide To a mixture of trichlorophenylphosphonium hexachlorophosphide (10.2 g, 22.3 mM) in the solvent phenylphosphonic dichloride (50 ml) was added benzoic acid (2.5 g, 22.3 mM). The reaction mixture was heated to 170° C. for 48 hours and worked-up as described above to give trichloromethyl benzene (4.2 g, 98 wt. % yield) as a yellow liquid.

What is claimed is:

1. A process for chlorinating a compound containing a carbon atom bonded to a hetero-atom selected from the group consisting of oxygen, nitrogen and sulfur wich comprises contacting the compound with a chloro phosphorus complex of the formula $$RP^{\oplus}Cl_3P^{\ominus}Cl_6$$

wherein R is selected from the group consisting of aryl, substituted aryl, alkyl and substituted alkyl so that the hetero-atom is replaced by at least one chlorine atom.

2. The process of claim 1 wherein the reaction takes place in the presence of a solvent.

3. The process of claim 1 wherein the hetero-atom is oxygen.

4. The process of claim 3 wherein the compound is selected from the group consisting of alcohols, carboxylic acids, ketones, aldehydes, acetals, ketals, ethers, epoxides, acid chlorides, esters and mixtures thereof.

5. The process of claim 1 wherein the hetero-atom is nitrogen.

6. The process of claim 5 wherein the compound is selected from the group consisting of nitro-aromatics, amides, and mixtures thereof.

7. The process of claim 6 wherein the nitroaromatic is nitrophthalic anhydride of the formula

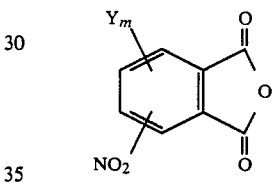

wherein m is selected from 0, 1, 2 and 3; and Y is selected independently each time it occurs from the group consisting of straight and branched chain alkyl, alkoxy and haloalkyl; and halogen.

8. The process of claim 7 wherein the anhydride is 3-nitrophthalic anhydride.

9. The process of claim 1 wherein the hetero-atom is sulfur.

10. The process of claim 9 wherein the compound is selected from the group consisting of thiols, sulfoxides, sulfones, sulfonates and sulfides.

* * * * *